United States Patent
Bicalho et al.

(10) Patent No.: US 9,700,586 B2
(45) Date of Patent: Jul. 11, 2017

(54) PROBIOTIC COMPOSITIONS AND METHODS

(71) Applicant: Cornell University, Ithaca, NY (US)

(72) Inventors: Rodrigo Carvalho Bicalho, Dryden, NY (US); Georgios Oikonomou, Ithaca, NY (US); Andre Gustavo Vieira Teixeira, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/380,881

(22) PCT Filed: Feb. 27, 2013

(86) PCT No.: PCT/US2013/028041
§ 371 (c)(1),
(2) Date: Aug. 25, 2014

(87) PCT Pub. No.: WO2013/130624
PCT Pub. Date: Sep. 6, 2013

(65) Prior Publication Data
US 2015/0044172 A1   Feb. 12, 2015

Related U.S. Application Data

(60) Provisional application No. 61/604,142, filed on Feb. 28, 2012.

(51) Int. Cl.
| | | |
|---|---|---|
| *A01N 63/00* | (2006.01) | |
| *A61K 35/74* | (2015.01) | |
| *C12Q 1/68* | (2006.01) | |
| *A23K 10/18* | (2016.01) | |
| *A23K 50/20* | (2016.01) | |
| *A23K 50/10* | (2016.01) | |
| *A23K 50/75* | (2016.01) | |
| *A23K 50/30* | (2016.01) | |
| *A23K 50/60* | (2016.01) | |

(52) U.S. Cl.
CPC .............. *A61K 35/74* (2013.01); *A23K 10/18* (2016.05); *A23K 50/10* (2016.05); *A23K 50/20* (2016.05); *A23K 50/30* (2016.05); *A23K 50/60* (2016.05); *A23K 50/75* (2016.05); *C12Q 1/689* (2013.01); *A23V 2200/3204* (2013.01); *C12Q 2600/118* (2013.01)

(58) Field of Classification Search
None
See application file for complete search history.

(56) References Cited

U.S. PATENT DOCUMENTS

| | | | |
|---|---|---|---|
| 8,697,052 B2 * | 4/2014 | Van Immerseel et al. | .. 424/93.4 |
| 2002/0127211 A1 | 9/2002 | Brassart et al. | |
| 2009/0053756 A1 | 2/2009 | Virkki et al. | |
| 2009/0075274 A1 | 3/2009 | Slepnev et al. | |
| 2010/0247489 A1 * | 9/2010 | Saur-Brosch | ................ 424/93.4 |
| 2012/0128821 A1 * | 5/2012 | Nazzaro et al. | ..... A23C 9/1234 426/34 |

FOREIGN PATENT DOCUMENTS

| | | |
|---|---|---|
| CN | 1269724 | 10/2001 |
| WO | 9902170 | 1/1999 |
| WO | 2011005756 | 1/2011 |
| WO | 2011140208 | 11/2011 |

OTHER PUBLICATIONS

Sokol et al. "Faecalibacterium prausnitzii is an anti-inflammatory commensal bacterium identified by gut microbiota analysis of Crohn disease patients". PNAS, Oct. 2008, vol. 105, No. 43, pp. 16731-16736.*
Donovan et al. "Growth and health of Holstein calves fed milk replacers supplemented with antibiotics or Enteroguard". J Dairy Sci., 2002, 85: 947-950.*
Timmerman et al. "Health and growth of veal calves fed milk replacers with or without probiotics". J Dairy Sci., 2005, 88: 2154-2165.*
Gorka et al. J Dairy Sci, 2011, 94, pp. 5578-5588.*
International Search Report corresponding to PCT/US2013/028041, mailed Aug. 27, 2013.

* cited by examiner

*Primary Examiner* — Vera Afremova
(74) *Attorney, Agent, or Firm* — Casimir Jones S.C.

(57) ABSTRACT

The present invention relates to probiotic compositions and methods of using such compositions. In particular, the present invention provides method of using *Faecalibacterium* spp. to improve weight gain, provide prophylaxis against diarrhea and/or improve feed efficiency in an animal.

17 Claims, 12 Drawing Sheets

PROBIOTIC COMPOSITIONS AND METHODS

CROSS-REFERENCE TO RELATED APPLICATIONS

This application is a U.S. 371 national stage entry of International Patent (PCT) Patent Application Serial No. PCT/US2013/028041, filed Feb. 27, 2013, which claims the benefit and priority to U.S. Provisional Patent Application Ser. No. 61/604,142, filed Feb. 28, 2012, the contents of each of which are hereby incorporated by reference for all purposes.

FIELD OF INVENTION

The present invention relates to probiotic compositions and methods of using such compositions. In particular, the present invention provides method of using *Faecalibacterium* spp. to improve weight gain, provide prophylaxis against diarrhea and/or improve feed efficiency in an animal.

BACKGROUND OF THE INVENTION

Gut microbiota is known to have a role in shaping key aspects of postnatal life, such as the development of the immune system (Mazmanian et al., (2005) Cell 122(1): 107-118; Peterson et al., (2007) Cell Host Microbe 2(5): 328-339), and influencing the host's physiology, including energy balance. Transplanting the gut microbiota from normal mice into germ-free recipients increased their body fat without any increase in food consumption, raising the possibility that the composition of the microbial community in the gut affects the amount of energy extracted from the diet (Backhed et al., (2004) Proc Natl Acad Sci USA 101(44): 15718-15723). There is at least one type of obesity-associated gut microbiome characterised by higher relative abundance of Firmicutes or a higher Firmicutes to Bacteroidetes ratio (Ley et al., (2005) Proc Natl Acad Sci USA 102(31): 11070-11075; Turnbaugh et al., (2006) Nature 444(7122): 1027-1031). The role of intestinal microbiota in disease has also been shown. Gut microbes serve their host by functioning as a key interface with the environment; for example, they can protect the host organism from pathogens that cause infectious diarrhea. A decreased diversity of fecal microbiota and specifically a reduced diversity of Firmicutes in Crohn disease patients has been reported (Manichanh et al., (2006) Gut 55(2): 205-211), while it was recently shown that *Faecalibacterium prausnitzii* displays anti-inflammatory action and can potentially be used for the treatment of this disease (Sokol et al., (2008) Proc Natl Acad Sci USA 105(43): 16731-16736).

Efficient growth of pre-weaned dairy calves together with low incidence of disease (especially diarrhea and pneumonia) are prerequisites for their optimal performance after weaning and contribute in the profitability of a dairy enterprise. For every 1 kg of pre-weaning average daily gain, milk yield increased by 1,113 kg in the first lactation (Soberon et al., (2012) J Dairy Sci 95(2): 783-793). The notion that calves' intestinal microbiota profiles are probably related with growth and disease already exists. Probiotics, bacteria with a beneficial effect on animals' intestinal health, have been found to have antidiarrheal capacities and enhance growth rates in calves (Donovan et al., (2002) J Dairy Sci 85(4): 947-950; Timmerman et al., (2005) J Dairy Sci 88(6): 2154-2165).

However, methods for preventing diarrhea and improving growth of newborn animals are still needed.

SUMMARY OF THE INVENTION

The present invention relates to probiotic compositions and methods of using such compositions. In particular, the present invention provides method of using *Faecalibacterium* spp. to improve weight gain, provide prophylaxis against diarrhea and/or improve feed efficiency in an animal.

For example, in some embodiments, the present invention provides a method of improving weight gain, providing prophylaxis against diarrhea and/or improving feed efficiency in an animal comprising administering said animal a composition comprising one or more *Faecalibacterium* spp. (e.g., including but not limited to, *Faecalibacterium prausnitzii*). In some embodiments, the composition comprises one or more *Faecalibacterium* spp. in an amount effective to improve weight gain, provide phophylaxis against diarrhea, and/or improve feed efficiency in the animal. The present invention is not limited to a particular animal. Examples include, but are not limited to, domestic animals (e.g., cattle (e.g., calf), sheep, swine, horses or poultry). In some embodiments, the animal is less than 1 week, one month, or two months of age. In some embodiments, the composition is formulated as a powder, bolus, gel, drench, or capsule. In some embodiments, the composition is provided as part of a milk replacer. In some embodiments, the composition is coadministered with at least a second probiotic organism (e.g., including but not limited to, *Lactobacillus acidophilus, L. lactis, L. plantarum, L. casei, Bacillus subtilis, B. licheniformis, Enterococcus faecium, Bifidobacterium bifidum, B. longum, B. thermophilum, Propionibacterium jensenii*, yeast, or combinations thereof). In some embodiments, the composition is formulated with an additional additive (e.g., including but not limited to, an energy substrate, a mineral, a vitamin, or combinations thereof).

Additional embodiments provide a probiotic composition comprising *Faecalibacterium* spp. in combination with a milk protein. In some embodiments, the composition is a powder or a milk replacer. In some embodiments, the composition further comprises an energy substrate, a mineral, a vitamin, or at least a second probiotic organism (e.g., including but not limited to, *Lactobacillus acidophilus, L. lactis, L. plantarum, L. casei, Bacillus subtilis, B. licheniformis, Enterococcus faecium, Bifidobacterium bifidum, B. longum, B. thermophilum, Propionibacterium jensenii*, and yeast, or combinations thereof).

The present invention further provides a probiotic composition for administration to a domestic animal comprising *Faecalibacterium* spp. in combination with an additional additive selected from, for example, an energy substrate, a mineral, a vitamin, at least a second probiotic organism (e.g., including but not limited to, *Lactobacillus acidophilus, L. lactis, L. plantarum, L. casei, Bacillus subtilis, B. licheniformis, Enterococcus faecium, Bifidobacterium bifidum, B. longum, B. thermophilum, Propionibacterium jensenii*, and yeast, or combinations thereof). In some embodiments, the composition is formulated as an oral delivery vehicle powder, bolus, gel, drench, or capsule, suitable for administration to a domestic animal. In some embodiments, the composition is provided in an amount effective to improve weight gain, improve feed efficiency, or provide prophylaxis against diarrhea in an animal.

The present invention also provides the use of any of the aforementioned compositions to improve weight gain, improve feed efficiency, or provide prophylaxis against diarrhea in an animal.

Further embodiments of the present invention provide a method of supplementing the diet of a domestic animal comprising adding a comprising comprising *Faecalibacterium* spp. to the diet of the domestic animal.

In some further embodiments, the present invention provides a method of providing a diagnosis or prognosis for a domestic animal comprising: contacting a sample from a domestic animal with a *Faecalibacterium* detection reagent and optionally a *Clostridium sensu stricto* spp. detection reagent; determining the amount, presence or absence of *Faecalibacterium* and/or *Clostridium sensu stricto* spp. in the sample; and using the determination of the amount, presence or absence of *Faecalibacterium* and/or *Clostridium sensu stricto* spp. in the sample to provide a diagnosis or prognosis (e.g., risk of diarrhea and/or level of intestinal health) in the domestic animal. In some embodiments, the *Clostridium sensu stricto* spp. is *Clostridium perfringens*. In some embodiments, the methods further comprises the step of using the determination to identify domestic animals or groups of domestic animals in need of supplementation with a probiotic composition comprising *Faecalibacterium* spp.

The present invention also provides a kit, comprising a *Faecalibacterium* detection reagent, and optionally a *Clostridium sensu stricto* spp. detection reagent.

Additional embodiments are described herein.

DEFINITIONS

Figure 1:
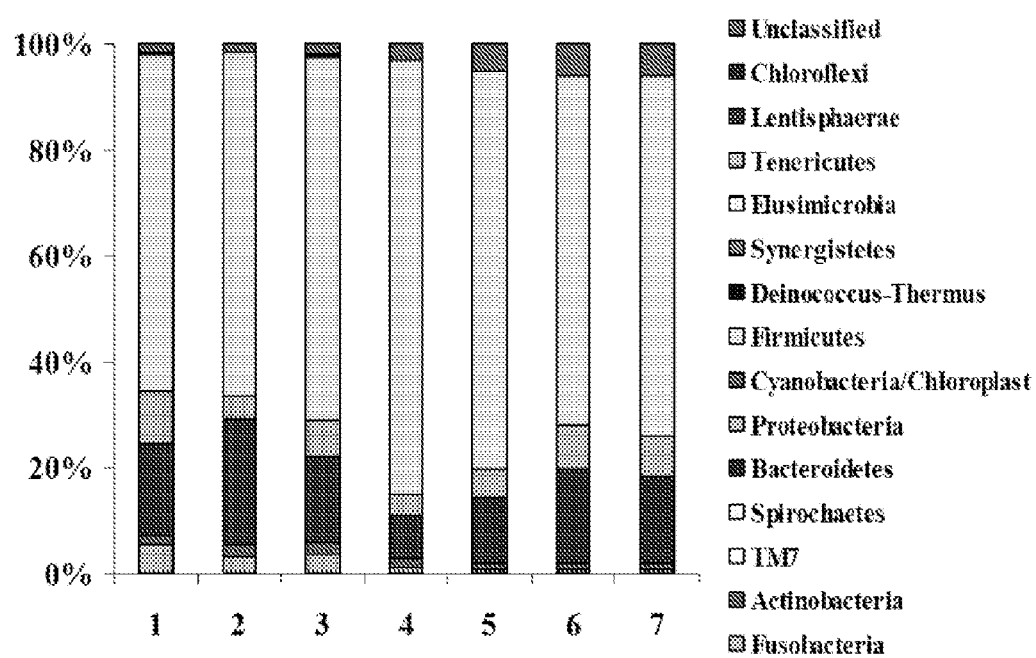
FIG. 1. Aggregate microbiota composition at phylum level by week of life.

To facilitate an understanding of the present invention, a number of terms and phrases are defined below:

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

As used herein, the term "prokaryotes" refers to a group of organisms that usually lack a cell nucleus or any other membrane-bound organelles. In some embodiments, prokaryotes are bacteria. The term "prokaryote" includes both archaea and eubacteria.

As used herein, the term "in vitro" refers to an artificial environment and to processes or reactions that occur within an artificial environment. In vitro environments can consist of, but are not limited to, test tubes, microtiter plates, and the like. The term "in vivo" refers to the natural environment (e.g., an animal or a cell) and to processes or reactions that occur within a natural environment.

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Such examples are not however to be construed as limiting the sample types applicable to the present invention.

Mammals are defined herein as all animals (e.g., human or non-human animals) that have mammary glands and produce milk.

As used herein, a "dairy animal" refers to a milk producing non-human mammal that is larger than a laboratory rodent (e.g., a mouse). In preferred embodiments, the dairy animals produce large volumes of milk and have long lactating periods (e.g., cows or goats).

A "subject" is an animal such as vertebrate, preferably a domestic animal or a mammal Mammals are understood to include, but are not limited to, murines, simians, humans, bovines, cervids, equines, porcines, canines, felines etc.

An "effective amount" is an amount sufficient to effect beneficial or desired results. An effective amount can be administered in one or more administrations, "Co-administration" refers to administration of more than one agent or therapy to a subject. Co-administration may be concurrent or, alternatively, the chemical compounds described herein may be administered in advance of or following the administration of the other agent(s). One skilled in the art can readily determine the appropriate dosage for co-administration. When co-administered with another therapeutic agent, both the agents may be used at lower dosages. Thus, co-administration is especially desirable where the claimed compounds are used to lower the requisite dosage of known toxic agents.

As used herein, the term "toxic" refers to any detrimental or harmful effects on a cell or tissue.

A "pharmaceutical composition" is intended to include the combination of an active agent with a carrier, inert or active, making the composition suitable for diagnostic or therapeutic use in vivo, in vivo or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, 15th Ed., Mack Publ. Co., Easton, Pa. (1975).

"Pharmaceutically acceptable salt" as used herein, relates to any pharmaceutically acceptable salt (acid or base) of a compound of the present invention, which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

As used herein, the term "nutraceutical," refers to a food substance or part of a food, which includes a probiotic bacterium. Nutraceuticals can provide medical or health benefits, including the prevention, treatment, or cure of a disorder.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms that are gram negative or gram positive. "Gram negative" and "gram positive" refer to staining patterns with the Gram-staining process that is well known in the art. (See e.g., Finegold and Martin, Diagnostic Microbiology, 6th Ed., CV Mosby St. Louis, pp. 13-15 [1982]). "Gram positive bacteria" are bacteria that retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

DETAILED DESCRIPTION OF THE INVENTION

The present invention relates to probiotic compositions and methods of using such compositions. In particular, the present invention provides method of using *Faecalibacterium* spp. to improve weight gain, provide prophylaxis against diarrhea and/or improve feed efficiency in an animal.

Metagenomics refers to culture-independent studies of the collective set of genomes of mixed microbial communities (Petrosino et al., (2009) Clin Chem 55(5): 856-866). Sequencing and analysis of hypervariable regions within the 16S rRNA gene can provide relatively rapid and cost effective methods for assessing bacterial diversity and abundance. Barcoded pyrosequencing on the Genome Sequencer FLX/454 Life Sciences platform enable a dramatic increase in throughput via parallel in-depth analysis of many samples with limited sample processing and lower costs. Edrington et al. (2012) (J Dairy Sci 95(8): 4519-4525) recently used pyrosequencing to describe the colonic microflora diversity of dairy calves fed waste milk. Such an approach can also be used to better depict the interplay between intestinal microbiota and neonatal calves' growth and disease resistance.

Experiments described herein used barcoded pyrosequencing to characterize the fecal microbiota of calves during the pre-weaning period (first seven weeks of life) and identify relationships of certain microbiota profiles with health and weight gain.

Experiments conducted during the course of development of embodiments of the present invention identified changes in the intestinal microbiota of neonatal dairy calves during the first seven weeks of their life. Firmicutes average prevalence was getting higher from the first until the fourth week of life and then progressively decreased again. A reverse pattern was observed for Bacteroidetes prevalence. It is possible that these alterations reflect the gradual adaptation of the calves' gastrointestinal track first to milk consumption and later to the consumption of solid feed. An observation made at genus level better support this assumption. *Lactobacillus* spp. (known to be related with digestion of milk) prevalence reached a 14.74% maximum during the fourth week of the calves' life and then progressively decreased to reach 2.15% during the seventh week. *Bifidobacterium* spp. prevalence (also known to be related with digestion of milk) showed a similar pattern. It is known that the consumption of solid feed by dairy calves significantly increases after the fourth week of the calves' life (Bach et al., (2007) J Dairy Sci 90(6): 3028-3033).

Microbial diversity of fecal samples was steadily increasing during the whole preweaning period and this is in agreement with findings presented by Edrington et al. (2012; supra). Chao1 index was lower during the third, fourth and fifth week of life in calves that suffered from pneumonia. All pneumonia cases were treated with parenteral administration of antibiotics and all of them were diagnosed after the first week of life. Antibiotics usage has been shown to affect intestinal microbiota profiles in humans (Claesson et al., (2011) Proc Natl Acad Sci USA 108 Suppl 1: 4586-4591) and swine (Looft et al., (2012) Proc Natl Acad Sci USA 109(5): 1691-1696). Diarrhea was also associated with a reduction of microbial diversity during the third week of life. It was recently reported that diversity of intestinal microbiota was reduced in human patients with diarrhea-predominant irritable bowel syndrome (Carroll et al., (2012) Neurogastroenterol Motil 24(6): 521-30, e248). Increased fecal microbial diversity was associated with higher weight gain.

Wu et al. (2012) reported that the bacterial composition of developing and mature rumen displayed a striking difference. This is also the case for the intestinal microbiota even during the short preweaning period. Using discriminant analysis it was shown that fecal microbiota was significantly different between samples obtained during the first week and samples obtained during the seventh week of the calves' life. Certain genera (*Comamonas, Alistipes, Bacteroides, Parabacteroides, Pelistega* and *Porphyromonas*) were found to have a higher prevalence after the fourth week of the calves' life and were significant for the discriminant analysis that discriminated samples from different weeks of the calves' life.

*Faecalibacterium* spp. prevalence during the first week of the calves' life was found in this study to be significantly associated with body weight gain during the preweaning period. Sequences representative of the *Faecalibacterium* spp in this study were found to match with *Faecalibacterium prausnitzii* sequences. Calves form the high prevalence tercile gained 20.3% more weight until they were weaned comparing to the low prevalence tercile ones. A recent study reported that the prevalence of *Faecalibacterium prausnitzii* in the feces of obese children was significantly higher than non-obese children indicating a potential energy harvesting role of this specific microorganism in the human gut (Balamurugan et al., (2010) Br J Nutr 103(3): 335-338).

*Faecalibacterium prausnitzii* is a butyrate producing microorganism. It has been reported that *Faecalibacterium prausnitzii* strains present in human faeces produced butyrate and in many strains this was associated with net consumption of acetate (Duncan et al., (2004) Br J Nutr 91(6): 915-923). Butyrate has the highest energy value per mol of the major rumen volatile fatty acids, is extensively metabolized by the rumen epithelium (Baldwin and McLeod (2000) J Anim Sci 78(3): 771-783) and exerts mitotic effects on the epithelium during development (Mentschel et al., (2001) Arch Tierernahr 55(2): 85-102). Additionally butyrate concentrations were found to be higher in the rumen fluid of steers that showed higher feed efficiency (Guan et al., (2008) FEMS Microbiol Lett 288(1): 85-91).

Calves with higher prevalence of *Faecalibacterium* spp. in the first week of life had significantly lower incidence of diarrhea during the first four weeks of their life. An anti-inflammatory effect of *Faecalibacterium prausnitzii*, partially due to secreted metabolites able to block NF-kB activation and IL-8 production was recently. Butyrate is a key mediator in the inflammatory process in the large intestine (Ley et al., 2005; supra; Turnbaugh et al., 2006; supra), while it is an important source of energy for colonic epithelial cells and may enhance the integrity of the epithelial barrier (Schwiertz et al., (2010) J Pediatr 157(2): 240-244.e1).

Accordingly, embodiments of the present invention provide probiotic compositions comprising *Faecalibacterium* species and uses of such compositions in treating and preventing intestinal disease in animals.

I. Compositions and Kits

In some embodiments, the present invention provides probiotic compositions and kits. In some embodiments, probiotic compositions comprise one or more *Faecalibacterium* spp. The present invention is not limited to a particular one or more *Faecalibacterium* spp. Examples include, but are not limited to, *Faecalibacterium prausnitzii*.

In some embodiments, compositions comprise one or more (e.g., 2 or more, 5 or more, 10 or more, etc.) additional strains of bacteria or other microorganisms (e.g., probiotic microorganisms). Examples include, but are not limited to, *Lactobacillus acidophilus, L. lactis, L. plantarum, L. casei, Bacillus subtilis, B. lichenformis, Enterococcus faecium, Bifidobacterium bifidum, B. longum, B. thermophilum, Propionibacterium jensenii*, yeast, or combinations thereof. In some embodiments, multiple strains of the same bacteria are utilized in combination.

In some embodiments, compositions comprise one or more additional components (e.g., including but not limited to, additional additive selected from the group consisting of an energy substrate, a mineral, a vitamin, or combinations thereof).

In some embodiments, bacteria are live cells or freeze-dried cells. Freeze-dried bacteria can be stored for several years with maintained viability. In certain applications, freeze-dried bacteria are sensitive to humidity. One way of protecting the bacterial cells is to store them in oil. The freeze dried bacterial cells can be mixed directly with a suitable oil, or alternately the bacterial cell solution can be mixed with an oil and freeze dried together, leaving the bacterial cells completely immersed in oil. Suitable oils may be edible oils such as olive oil, rapeseed oil which is prepared conventionally or cold-pressed, sunflower oil, soy oil, maize oil, cotton-seed oil, peanut oil, sesame oil, cereal germ oil such as wheat germ oil, grape kernel oil, palm oil and palm kernel oil, linseed oil. The viability of freeze-dried bacteria in oil is maintained for at least nine months. Optionally live cells can be added to one of the above oils and stored.

In some embodiments, the compositions are part of a milk replacer (e.g., for administration to a neonatal or young animal). In some embodiments, compositions comprise one or more probiotic bacteria as described herein in combination with a milk protein (e.g., caseins or whey proteins).

In some embodiments, compositions are added to nutraceuticals, food products, or foods. In some embodiments, to give the composition or nutraceutical a pleasant taste, flavoring substances such as for example mints, fruit juices, licorice, *Stevia rebaudiana*, steviosides or other calorie free sweeteners, rebaudioside A, essential oils like *eucalyptus* oil, or menthol can optionally be included in compositions of embodiments of the present invention.

In some compositions embodiments, compositions are formulated in pharmaceutical compositions. The bacteria of embodiments of the invention may be administered alone or in combination with pharmaceutically acceptable carriers or diluents, and such administration may be carried out in single or multiple doses.

Compositions may, for example, be in the form of tablets, resolvable tablets, capsules, bolus, drench, pills sachets, vials, hard or soft capsules, aqueous or oily suspensions, aqueous or oily solutions, emulsions, powders, granules, syrups, elixirs, lozenges, reconstitutable powders, liquid preparations, creams, troches, hard candies, sprays, chewing-gums, creams, salves, jellies, gels, pastes, toothpastes, rinses, dental floss and tooth-picks, liquid aerosols, dry powder formulations, HFA aerosols or organic or inorganic acid addition salts.

The pharmaceutical compositions of embodiments of the invention may be in a form suitable for oral, topical, buccal administration. Depending upon the disorder and patient to be treated and the route of administration, the compositions may be administered at varying doses.

For oral or buccal administration, bacteria of embodiments of the present invention may be combined with various excipients. Solid pharmaceutical preparations for oral administration often include binding agents (for example syrups, *acacia*, gelatin, tragacanth, polyvinylpyrrolidone, sodium lauryl sulphate, pregelatinized maize starch, hydroxypropyl methylcellulose, starches, modified starches, gum *acacia*, gum tragacanth, guar gum, pectin, wax binders, microcrystalline cellulose, methylcellulose, carboxymethylcellulose, hydroxypropyl methylcellulose, hydroxyethyl cellulose, hydroxypropyl cellulose, copolyvidone and sodium alginate), disintegrants (such as starch and preferably corn, potato or tapioca starch, alginic acid and certain complex silicates, polyvinylpyrrolidone, gelatin, *acacia*, sodium starch glycollate, microcrystalline cellulose, crosscarmellose sodium, crospovidone, hydroxypropyl methylcellulose and hydroxypropyl cellulose), lubricating agents (such as magnesium stearate, sodium lauryl sulfate, talc, silica polyethylene glycol waxes, stearic acid, palmitic acid, calcium stearate, carnuba wax, hydrogenated vegetable oils, mineral oils, polyethylene glycols and sodium stearyl fumarate) and fillers (including high molecular weight polyethylene glycols, lactose, calcium phosphate, glycine magnesium stearate, starch, rice flour, chalk, gelatin, microcrystalline cellulose, calcium sulphate, and lactitol). Such preparations may also include preservative agents and antioxidants.

Liquid compositions for oral administration may be in the form of, for example, emulsions, syrups, or elixirs, or may be presented as a dry product for reconstitution with water or other suitable vehicle before use. Such liquid compositions may contain conventional additives such as suspending agents (e.g. syrup, methyl cellulose, hydrogenated edible fats, gelatin, hydroxyalkylcelluloses, carboxymethylcellulose, aluminium stearate gel, hydrogenated edible fats) emulsifying agents (e.g. lecithin, sorbitan monooleate, or *acacia*), aqueous or non-aqueous vehicles (including edible oils, e.g. almond oil, fractionated coconut oil) oily esters (for example esters of glycerine, propylene glycol, polyethylene glycol or ethyl alcohol), glycerine, water or normal saline; preservatives (e.g. methyl or propyl p-hydroxybenzoate or sorbic acid) and conventional flavouring, preservative, sweetening or colouring agents. Diluents such as water, ethanol, propylene glycol, glycerin and combinations thereof may also be included.

Other suitable fillers, binders, disintegrants, lubricants and additional excipients are well known to a person skilled in the art.

In some embodiments, bacteria are spray-dried. In other embodiments, bacteria re suspended in an oil phase and are encased by at least one protective layer, which is water-soluble (water-soluble derivatives of cellulose or starch, gums or pectins; See e.g., EP 0 180 743, herein incorporated by reference in its entirety).

In some embodiments, the present invention provides kits, pharmaceutical compositions, or other delivery systems for use in improving weight gain, providing prophylaxis against diarrhea and/or improving feed efficiency in an animal. The kit may include any and all components necessary, useful or sufficient for research or therapeutic uses including, but not limited to, one or more probiotic bacteria, pharmaceutical carriers, and additional components useful, necessary or sufficient for improving weight gain, providing prophylaxis against diarrhea and/or improving feed efficiency in an animal. In some embodiments, the kits provide a sub-set of the required components, wherein it is expected that the user will supply the remaining components. In some embodiments, the kits comprise two or more separate containers wherein each container houses a subset of the components to be delivered.

Optionally, compositions and kits comprise other active components in order to achieve desired therapeutic effects.

II. Therapeutic and Supplement Uses

Embodiments of the present invention provide compositions comprising probiotic bacteria (e.g., *Faecalibacterium* spp. alone or in combination with additional probiotic bacteria) (e.g., pharmaceutical, nutraceutical, or food compositions) for use in improving the health of an animal. In some embodiments, compositions improve weight gain, provide prophylaxis against diarrhea and/or improve feed efficiency in an animal. In some embodiments, the animal is a domestic or agricultural animal (e.g., cow, sheep, goat, pig, etc.). In some embodiments, the animal is neonatal, newborn, or young. For example, in some embodiments, the animal is one day, 2, days, 3, days, 4 days, 5 days, 6 days, 1 week, 2 weeks, 3 weeks, one month, or 2 months of age, although other ages are specifically contemplated.

In some embodiments, compositions comprising probiotic bacteria are administered once to an animal in need thereof. In other embodiments, compositions are administered on an ongoing, recurrent, or repeat basis (e.g., multiple times a day, once a day, once every 2, 3, 4, 5, or 6 days, once a week, etc.) for a period of time (e.g., multiple days, months, or weeks). Suitable dosages and dosing schedules are determined by one of skill in the art using suitable methods (e.g., those described in the experimental section below or known to one of skill in the art).

III. Diagnostic and Prognostic Applications

In some embodiments, the present invention provides compositions and methods for research, screening, and diagnostic applications. For example, in some embodiments, diagnostic applications provide a risk or diarrhea or a measure of intestinal health. In some embodiments, the level, presence or absence of *Faecalibacterium* and/or *Clostridium sensu stricto* spp, is used to provide a diagnosis or prognosis. For example in some embodiments, a lack of or decreased level of *Faecalibacterium* and/or *Clostridium sensu stricto* spp is associate with an increased risk of diarrhea and decreased intestinal health.

In some embodiments, animals identified as being at increased risk of diarrhea or decreased intestinal health are administered probiotic compositions (e.g., comprising *Faecalibacterium* spp.).

Exemplary diagnostic methods are described herein. In some embodiments, intact bacteria are detected (e.g., by detecting surface polypeptides or markers). In other embodiments, bacteria are lysed and nucleic acids or proteins (e.g., corresponding to genes specific to the species of bacteria) are detected.

a. Nucleic Acid Detection

In some embodiments, bacteria are identified using detection reagents that specifically interact with a nucleic acid that identifies a particular species of bacteria (e.g., *Faecalibacterium* and/or *Clostridium sensu stricto* spp). Exemplary detection reagents and detection methods are described below.

1. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

The methods disclosed herein can comprise transcriptome sequencing (e.g., RNA-Seq). Sequencing can comprise platforms such as the Illumina GenomeAnalyzer platform, ABI Solid Sequencing or Life Science's 454 Sequencing. Alternatively, sequencing comprises Helicos' Direct RNA Sequencing (DRS™) technology. The sequencing reactions may comprise capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis may comprise reversible terminator sequencing, processive single molecule sequencing, sequential nucleotide flow sequencing, or a combination thereof. Sequential nucleotide flow sequencing may comprise pyrosequencing, pH-mediated sequencing, semiconductor sequencing or a combination thereof. Conducting one or more sequencing reactions comprises whole genome sequencing or exome sequencing.

In some embodiments, nucleic acid sequencing methods are utilized for detection. In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics*, 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are described, including fluorescence-based sequencing methodologies (See, e.g., Birren et al., Genome Analysis: Analyzing DNA, 1, Cold Spring Harbor, N.Y.; herein incorporated by reference in its entirety). In some embodiments, automated sequencing techniques are utilized. In some embodiments, parallel sequencing of partitioned amplicons (PCT Publication No: WO2006084132 to Kevin McKernan et al., herein incorporated by reference in its entirety) is utilized. In some embodiments, DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties) is utilized. Additional examples of sequencing techniques include Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbial.*, 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbial.*, 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5):1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., *Clinical Chem.*, 55: 641-658, 2009; MacLean et al., *Nature Rev. Microbiol.*, 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

In some embodiments, the nucleic acid sequencing approach developed by Stratos Genomics, Inc. (e.g., Xpandomers) is utilized. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectable fluorescence resonance energy transfer (FRET) upon nucleotide addition.

2. Hybridization

Illustrative non-limiting examples of nucleic acid hybridization techniques include, but are not limited to, in situ hybridization (ISH), microarray, and Southern or Northern blot.

In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, nucleic acids are detected using fluorescence in situ hybridization (FISH). In some embodiments, FISH assays utilize bacterial artificial chromosomes (BACs). These have been used extensively in the human genome sequencing project (see Nature 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on one or more bacterial cells. Specific protocols are obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., Am. J. Hum. Genet. 49:112-119 (1991); Klinger, et al., Am. J. Hum. Genet. 51:55-65 (1992); and Ward, et al., Am. J. Hum. Genet. 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121,489 and 6,573,043. All of these references are hereby incorporated by reference in their entirety and may be used along with similar references in the art and with the information provided in the Examples section herein to establish procedural steps convenient for a particular laboratory.

The one or more nucleic acids may be detected by conducting one or more hybridization reactions. The one or more hybridization reactions may comprise one or more hybridization arrays, hybridization reactions, hybridization chain reactions, isothermal hybridization reactions, nucleic acid hybridization reactions, or a combination thereof. The one or more hybridization arrays may comprise hybridization array genotyping, hybridization array proportional sensing, DNA hybridization arrays, macroarrays, microarrays, high-density oligonucleotide arrays, genomic hybridization arrays, comparative hybridization arrays, or a combination thereof.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

4. Amplification

The methods disclosed herein may comprise conducting one or more amplification reactions. Nucleic acids may be amplified prior to or simultaneous with detection. Conducting one or more amplification reactions may comprise one or more PCR-based amplifications, non-PCR based amplifications, or a combination thereof. Illustrative non-limiting examples of nucleic acid amplification techniques include, but are not limited to, polymerase chain reaction (PCR), reverse transcription polymerase chain reaction (RT-PCR), nested PCR, linear amplification, multiple displacement amplification (MDA), real-time SDA, rolling circle amplification, circle-to-circle amplification transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., Meth. Enzymol. 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., *Proc. Natl. Acad. Sci. USA* 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

5. Detection Methods

Non-amplified or amplified nucleic acids can be detected by any conventional means. For example, the nucleic acids can be detected by hybridization with a detectably labeled probe and measurement of the resulting hybrids. In another example, the nucleic acids are detected by sequencing. Illustrative non-limiting examples of detection methods are described herein.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety). Additional detection methods may include microarrays and electrophoresis (e.g., gel electrophoresis). Detection methods can be quantitative or semi-quantitative. Detection methods may also comprise the use of one or more labels (e.g., radioisotopes, fluorophores, chemiluminophores, enzymes, colloidal particles, and fluorescent microparticles, as well as antigens, antibodies, haptens, avidin/streptavidin, biotin, haptens, or enzyme cofactors/substrates, enzymes).

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

B. Polypeptide Detection

In some embodiments, polypeptides associated with a genus, species, or strain of bacteria are detected. Protein expression may be detected by any suitable method. In some embodiments, proteins are detected by their binding to an antibody (e.g., monoclonal or polyclonal antibody) raised against the protein.

Antibody binding is detected by techniques (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In some embodiments, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated.

In other embodiments, the immunoassay described in U.S. Pat. Nos. 5,599,677 and 5,672,480; each of which is herein incorporated by reference.

EXPERIMENTAL

The following examples are provided in order to demonstrate and further illustrate certain preferred embodiments and aspects of the present invention and are not to be construed as limiting the scope thereof.

Example 1

*Faecalibacterium* Prausnitzii is Associated with Enhanced Weight Gain and Improved Gastrointestinal Health in Neonatal Dairy Calves Materials and Methods
Farm and Management Fecal sample collection was conducted in a commercial dairy farm located near Ithaca, N.Y. and 61 Holstein, female calves were enrolled in the study. Standard husbandry practices were followed. Once weekly, calf health was assessed visually by using objective criteria of appetite, fecal consistency, hydration status, respiratory effort, and attitude. The body weight of the calves was measured at birth and weekly until weaning; a Waypig 15, 62" digital scale (Vittetoe inc., Keota, Iowa) was used. Together with the weekly weight measurements a fecal swamp was obtained by each calf and was frozen until used for extraction of bacterial DNA. The research protocol was reviewed and approved by the Institutional Animal Care and Use Committee of Cornell University.

DNA Extraction

Each fecal swab was placed in 2 ml of sterile PBS and was vortexed for at least two minutes. The swab was then removed and the sample was then centrifuged for 10 min at 13200 rpm. The supernatant was discarded and the remained pellet was resuspended in 400 µl of nuclease-free water. Isolation of microbial genomic DNA was then performed by using a QIAamp DNA minikit (Qiagen) according to the manufacturer's instructions. Some convenient modifications, such as the addition of 400 µg of lysozyme and incubation for 12 h at 56° C., were included to maximize bacterial DNA extraction. The DNA concentration and purity were evaluated by optical density using a NanoDrop ND-1000 spectrophotometer (NanoDrop Technologies, Rockland, Del., USA) at wavelengths of 230, 260 and 280 nm.

PCR Amplification of the V1-2 Region of Bacterial 16S rRNA Genes.

The 16S rRNA genes were individually amplified from each sample using a composite pair of primers containing unique 10-base barcode, which was used to tag the PCR products from respective samples. The forward primer used was 5'-CGTATCGCCTCCCTCGCGCCATCA-GNNNNNNNNNN<u>TC</u>AGAGTTTGATCC TGGCTCAG-3' (SEQ ID NO:1): the bold sequence is the GS FLX Titanium Primer A, and the italicized sequence is the universal broadly conserved bacterial primer 27F. The reversed primer used was 5'-CTATGCGCCTTGCCAGCCCGCTCA-GNNNNNNNNNN<u>CA</u>TGCTGCCTCCCG TAGGAGT-3' (SEQ ID NO:2): the bold sequence is the GS FLX Titanium Primer B, and the italicized sequence is the broad-range bacterial primer 338R. The sequence NNNNNNNNNN, which is identical in the forward and reverse primer of each pair, designates the unique 10-base barcode used to tag each PCR product. A two-base linker sequence (underlined) was inserted between the barcode and the template-specific sequence to help diminish any effect the composite primer might have on the efficiency of the amplifications. PCR were carried out in triplicates 20-µl reactions containing 0.3 µM forward and reverse primers, approximately 50 ng of template DNA and 10 µl HotStar Taq Plus Mix kit (Qiagen). A modified touchdown thermal cycling was used for amplification and consisted of initial denaturation at 95° C. for 2 min, followed by 30 cycles of denaturation at 95° C. for 30 sec, annealing (starting at 68° C. and subsequently decreased by 2° C./2 cycles until it reached 58° C., temperature at which the 20 remaining cycles were performed) for 30 sec, extension at 72° C. for 60 sec, and a final extension at 72° C. for 7 min. Replicate amplicons were pooled, purified with the QIAquick PCR Purification Kit (Qiagen), and visualized by electrophoresis using 1.2% (wt/vol) agarose gels stained with 0.5 µg/ml ethidium bromide before sequencing. Blank controls, in which no DNA was added to the reaction, were performed similarly and, since these failed to produce visible PCR products, they were not analyzed further.

Barcoded Pyrosequencing of the Bacterial 16S rRNA Genes.

Amplicons were quantified using the Quant-iT PicoGreen dsDNA Assay Kit (Invitrogen) and combined in equimolar ratios into a single tube. Pyrosequencing of the samples was carried at the Cornell University Life Sciences Core Laboratories Center using Roche 454 GS-FLX System Titanium Chemistry.

Obtained Sequences Analysis

The obtained FASTA sequences file was uploaded in the Ribosomal Database Project (RDP) pipeline initial processor that trimmed the 16S primers, tag sorted the sequences, and filtered out additional sequences of low-quality. RDP Classifier at the RDP's Pyrosequencing Pipeline was used to assign 16S rRNA gene sequences of each sample to the new phylogenetically consistent higher-order bacterial taxonomy (Wang et al., (2007) Appl Environ Microbiol 73(16): 5261-5267). The produced FASTA files were also uploaded in the RDP's aligner, which aligns the sequences using the INFERNAL aligner, a Stochastic Context Free Grammar (SCFG)-based, secondary-structure aware aligner (Nawrocki and Eddy (2007) PLoS Comput Biol 3(3): e56), and then processed by the complete linkage clustering tool (that clustered the aligned sequences in OTU). The cluster file that was obtained from the above described process was subsequently used for the evaluation of the samples richness and diversity through the estimation of Shannon and Chao1 indices, again using the RDP pyrosequencing pipeline (Wang et al., 2007; supra). The Shannon index is a nonparametric diversity index that combines estimates of richness (the total number of OTUs) and evenness (the relative abundance of OTUs). For example, communities with one dominant species have a low index, whereas communities with a more even distribution have a higher index. Chao1 is a nonparametric estimator of the minimum richness (number of OTUs) and is based on the number of rare OTUs (singletons and doublets) within a sample. The same cluster files were also used to obtain rarefaction curves for each sample, again using the RDP pyrosequencing pipeline.

In order to select representative sequences for *Faecalibacterium* spp. that was found to have significant effects on weight gain and diarrhea, the following procedure was used. The original FASTA file containing all the sequences was uploaded in the RDP pipeline initial processor that trimmed the 16S primers and filtered out additional sequences of low-quality. The produced file was uploaded in the RDP's aligner, which aligns the sequences using the INFERNAL aligner, a Stochastic Context Free Grammar (SCFG)-based, secondary-structure aware aligner (Nawrocki et al., supra), and then processed by the complete linkage clustering tool that clustered the aligned sequences in Operational Taxonomic Units (OTU). Finally, the dereplicate function was used to create one representative sequence for each OTU. Eventually, a new file of representative sequences was created and the RDP classifier was used again to classify them. Sequences classified as *Faecalibacterium* spp. were selected and the Basic Local Alignment Search Tool (BLASTn algorithm) from the National Center for Biotechnology Information (NCBI) web pages was then used to examine the nucleotide collection (EMBL/GenBank/DDBJ/PDB) databases for sequences with high similarity to these representative sequences (Altschul et al., (1990) J Mol Biol 215(3): 403-410).

Statistical Analysis

Discriminant analysis was performed in JMP Pro (SAS Institute Inc. North Carolina) using the bacterial genus prevalence as covariates and week of life as the categorical variable. This way the microbial transition from week one until week seven was illustrated. Discriminant analysis was also used to describe differences between samples' fecal microbiome by weight gain group during the first and second week of the calves' life. Bacterial genus prevalence was used as covariates and the interaction of week (1 and 2) and weight gain (low and high) as the categorical variable. Finally, discriminant analysis was used to describe differences between samples' fecal microbiome during the first week of the calves' life by diarrhea incidence. Bacterial genus prevalence was used as covariates and diarrhea incidence during the preweaning period as the categorical variable.

Prevalence of genera that were found to be significant for the discriminant analysis that discriminated high and low weight gain groups of calves or were found to be significant for the discriminant analysis that discriminated healthy and diarrheic calves was further analysed. MedCalc was used to create terciles for each genus that were subsequently used as class variables in multivariable models. Effects on weekly weight measurements were evaluated with the use of a mixed general linear model using the MIXED procedure of SAS. Body weight at birth and different genera prevalence terciles were offered to the Model. Body weight measurements were longitudinally collected and therefore treated as a repeated measurement; the error term was modeled by imposing a first-order autoregressive covariance structure to account appropriately for the within-calf correlation of milk measurements. Similar models were used to evaluate the differences in diversity indices for calves that had or did not have pneumonia or diarrhea and for calves that belonged to the high or the low weight gain group. Diarrhea incidence was estimated for the first four weeks of the calves' life. Effects on diarrhea incidence during the first four weeks of the calves' life were evaluated with the use of a logistic regression model that was fitted to the data using the GLIMMIX procedure of SAS. Genera prevalence terciles and body weight at birth were offered to the model. Only variables that were found to be significant ($P<0.05$) were retained in the above described Models.

Results

The mean prevalence of each microbial phylum by week of the calves' life (from the first until the seventh week) is presented in FIG. 1. Firmicutes was the major phylum, showing a prevalence that ranged from 63.84% to 81.90%, followed by Bacteroidetes (8.36% to 23.93%), *Proteobacteria* (3.72% to 9.75%), *Fusobacteria* (0.76% to 5.67%), and *Actinobacteria* (1.02% to 2.35%). The Firmicutes to Bacteroidetes ratio for these seven weeks ranged from 6.15 to 46.07.

Figure 2:
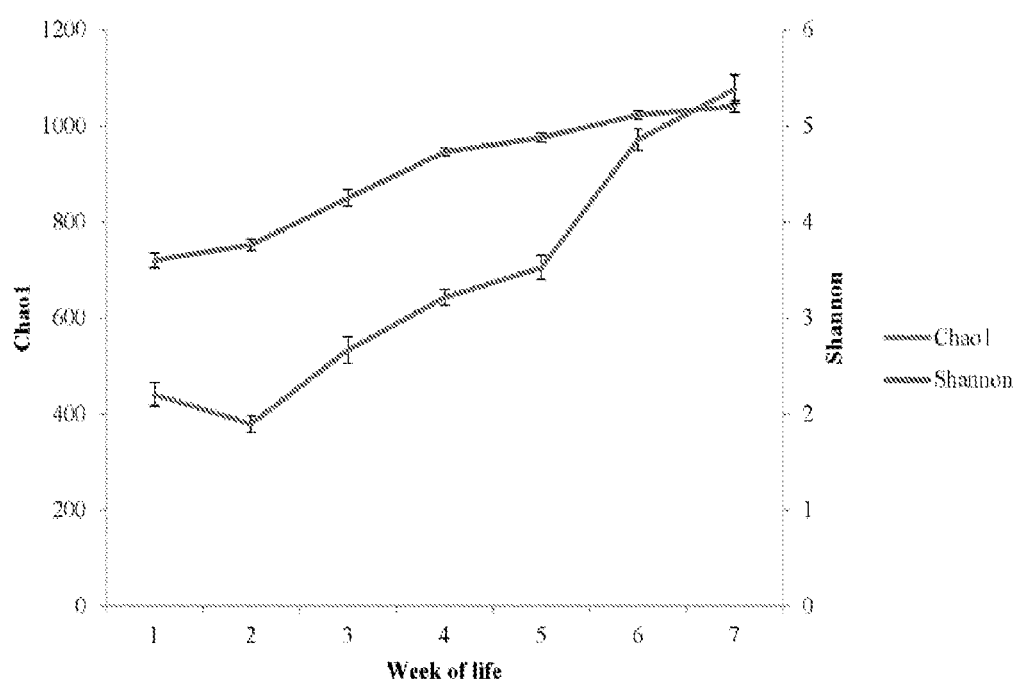
FIG. 2. Mean (±SEM) Chao1 and Shannon indices by week of life.
Figure 3:
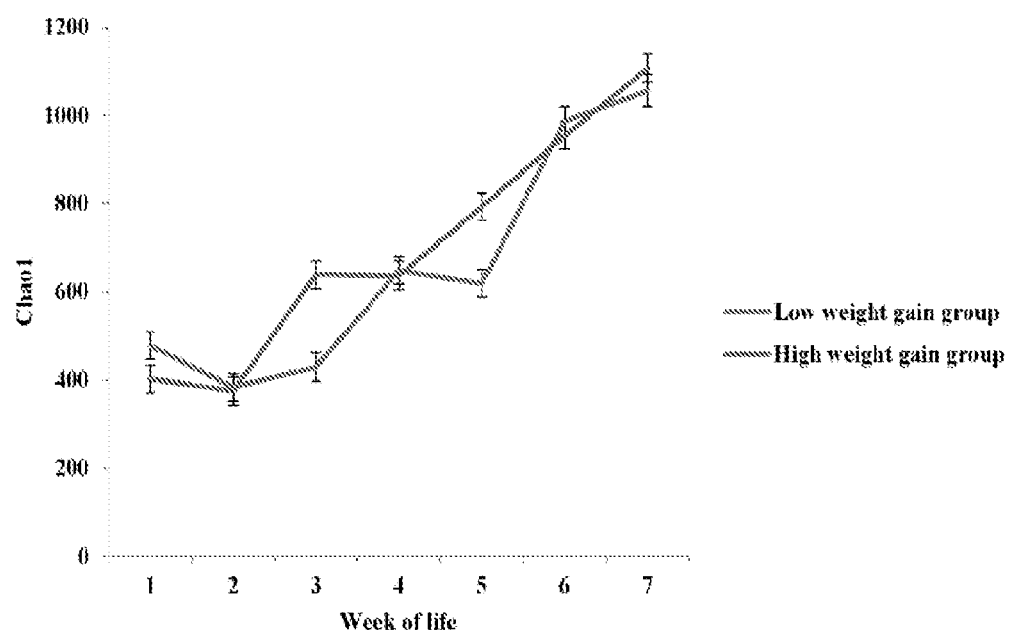
FIG. 3. Adjusted least square means (±SEM) of Chao1 and Shannon indices for each week of the calves' life and for the different weight gain groups.
Figure 3:
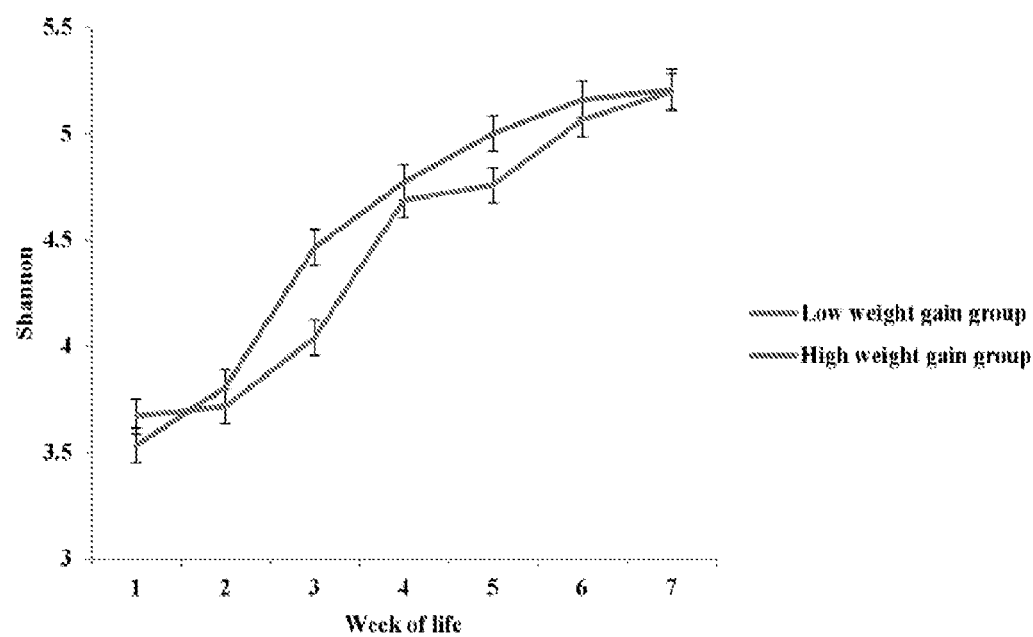
Figure 4:
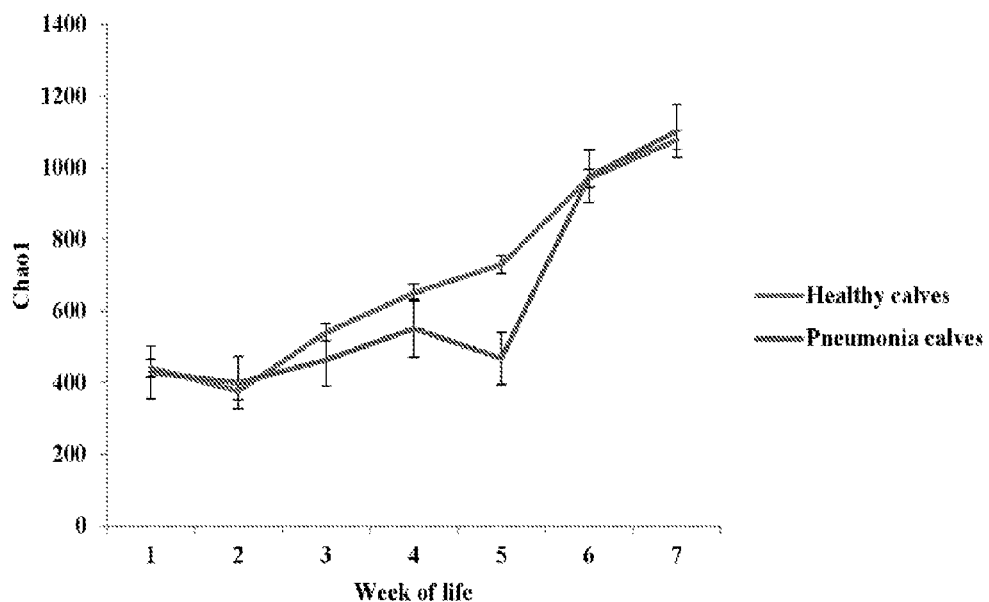
FIG. 4. Adjusted least square means (±SEM) of Chao1 index for each week of the calves' life and for calves that had or did not have pneumonia or diarrhea.
Figure 4:
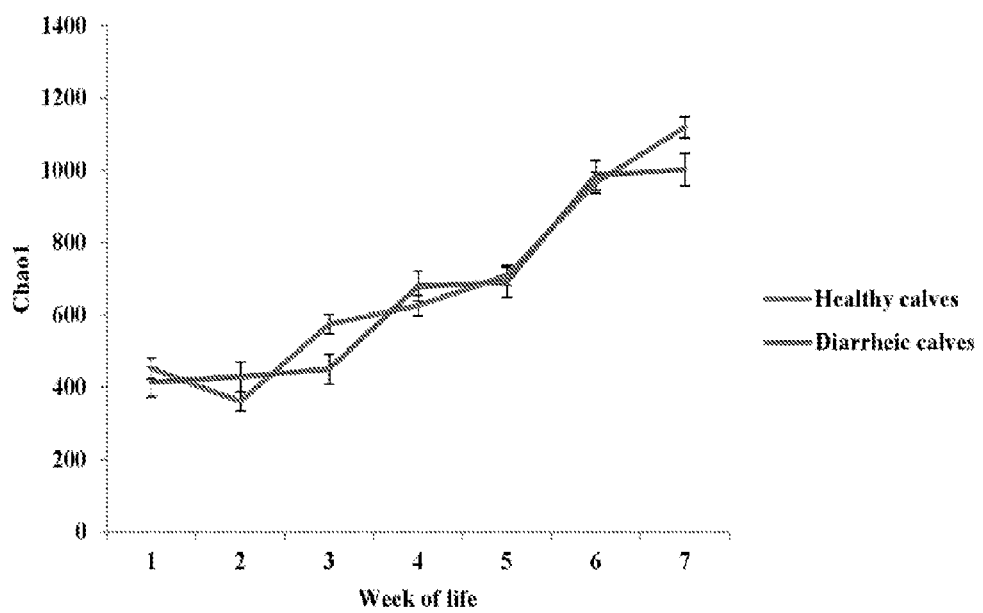
Figure 5:
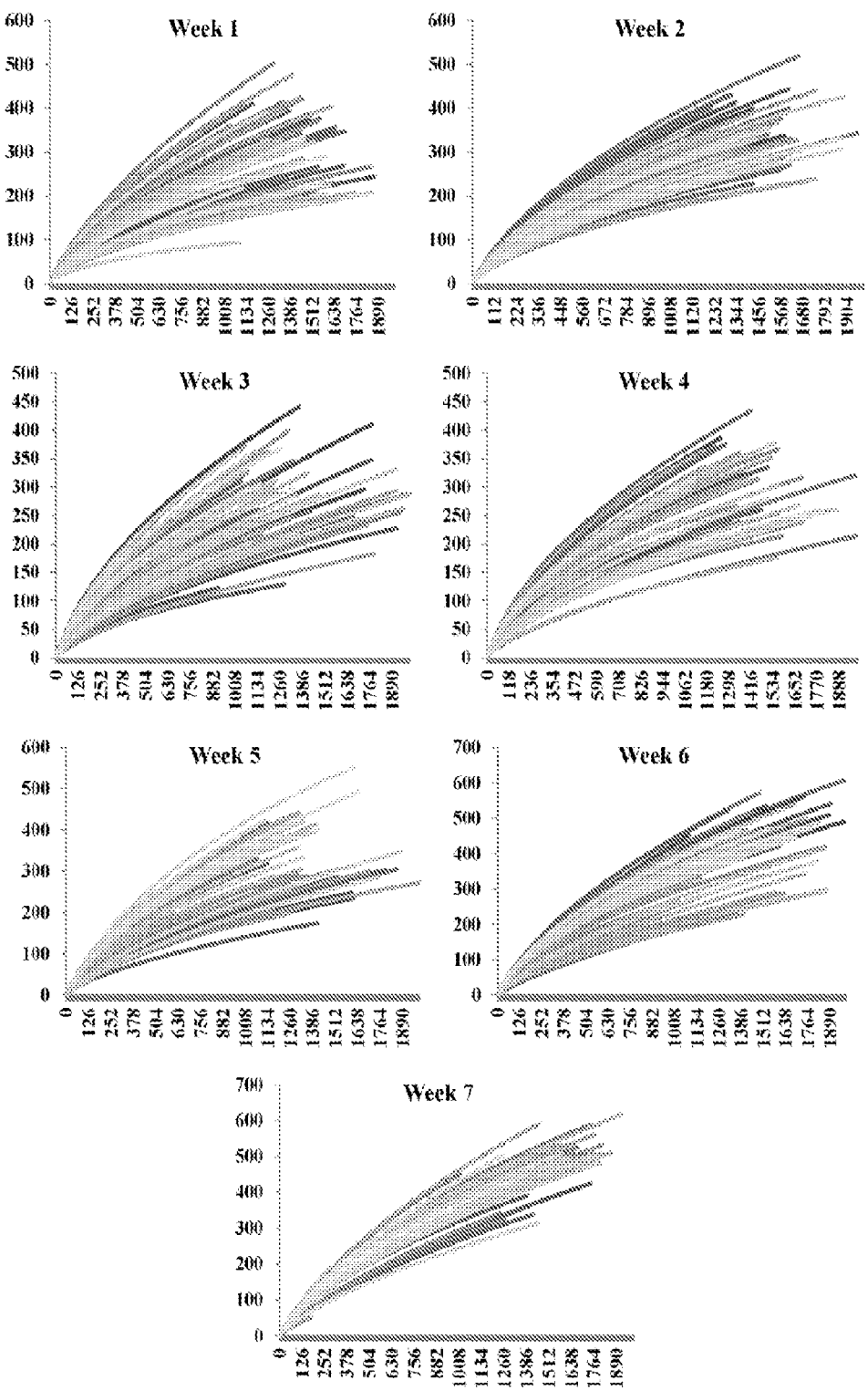
FIG. 5. Rarefaction curves of the fecal samples microbial community by week of life. Operational taxonomic units (OTU) at a 0.03 distance level.

Mean Chao1 and Shannon indices for each week of the calves' life are presented in FIG. 2. Both bacterial diversity indices were gradually increasing from the first to the seventh week of the calves' life. Adjusted least square means of Chao1 and Shannon indices for each week of the calves' life and for the different weight gain groups are presented in FIG. 3. Adjusted least square means of Chao1 index for each week of the calves' life and for calves that had or did not have pneumonia or diarrhea are presented in FIG. 4. Results regarding rarefaction analysis that was performed at OTU level for each different week of the calves' life are presented in FIG. 5.

Figure 6:
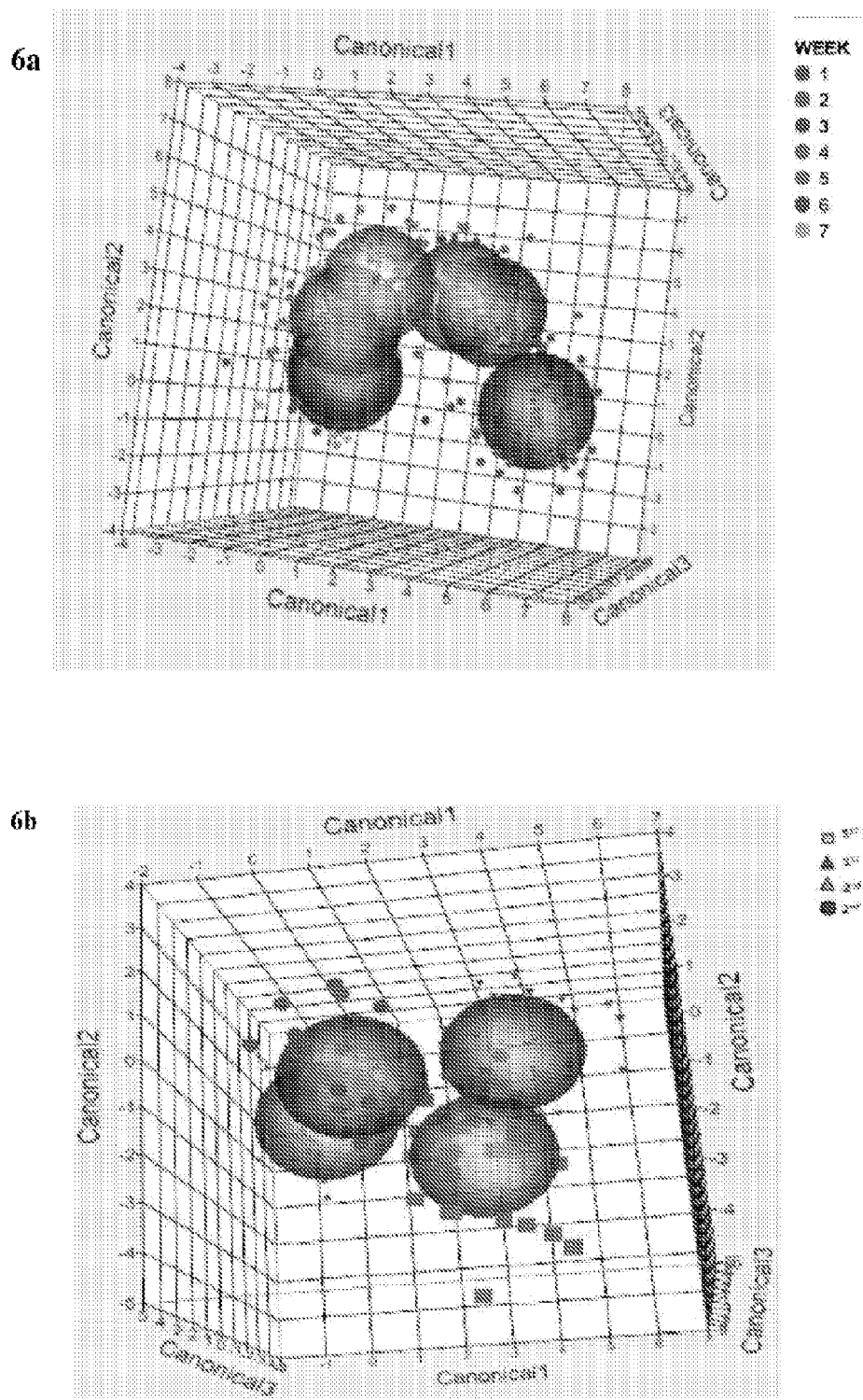
FIG. 6. 6a. Discriminant analysis of fecal microbiome by week of life. 6b Discriminant analysis of fecal microbiome by weight gain group and first and second week of life.
Figure 7:
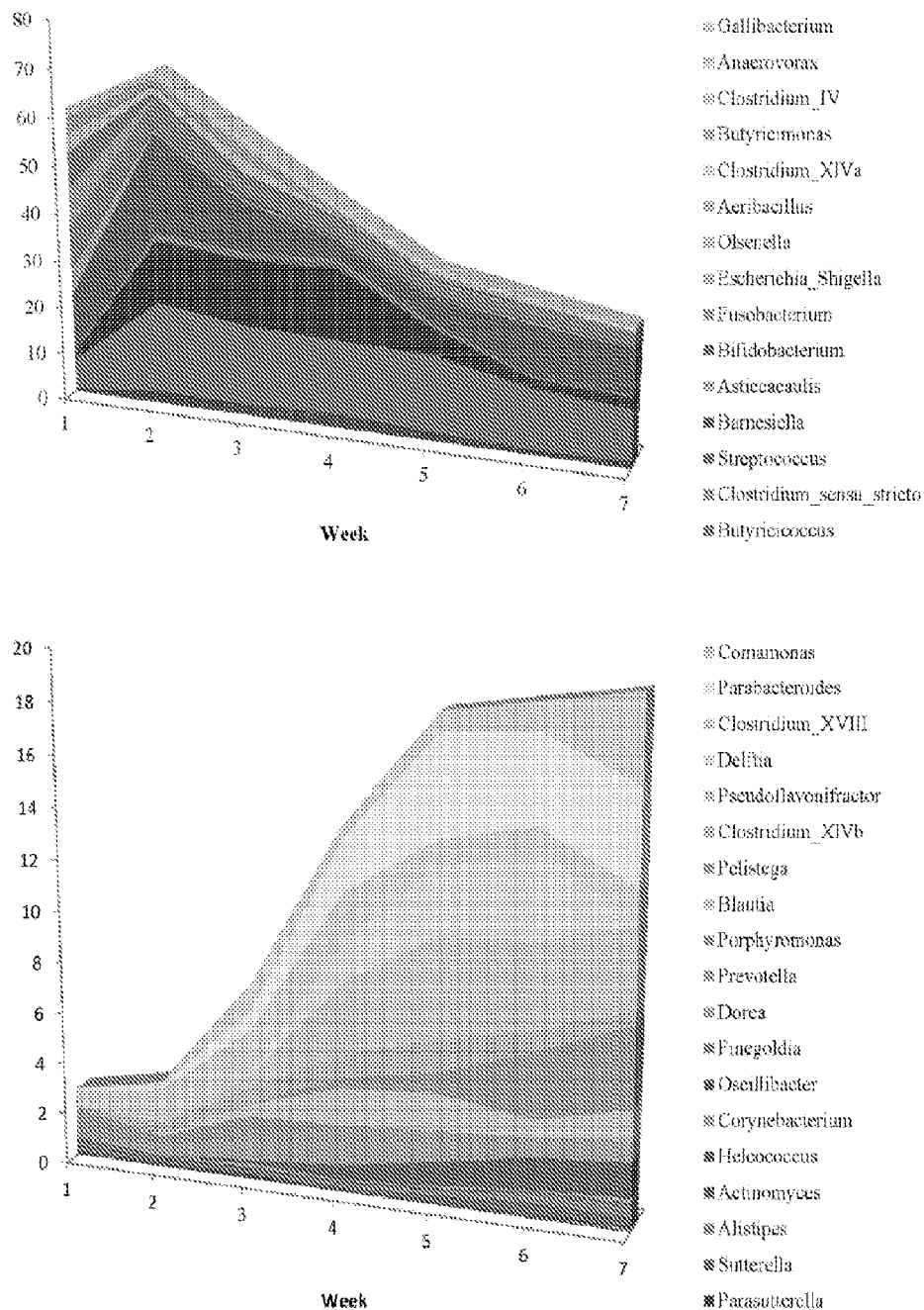
FIG. 7. Prevalence of genera that were found to be significant for the discriminant analysis of fecal microbiome by week of life.

The microbial transition from week one until week seven derived from the discriminant analysis that used bacterial genus prevalence as covariates and week of life as the categorical variable is illustrated in FIG. 6a. Prevalence of genera that were found to be significant for this analysis by week of the calves' life is presented in FIG. 7.

Figure 8:
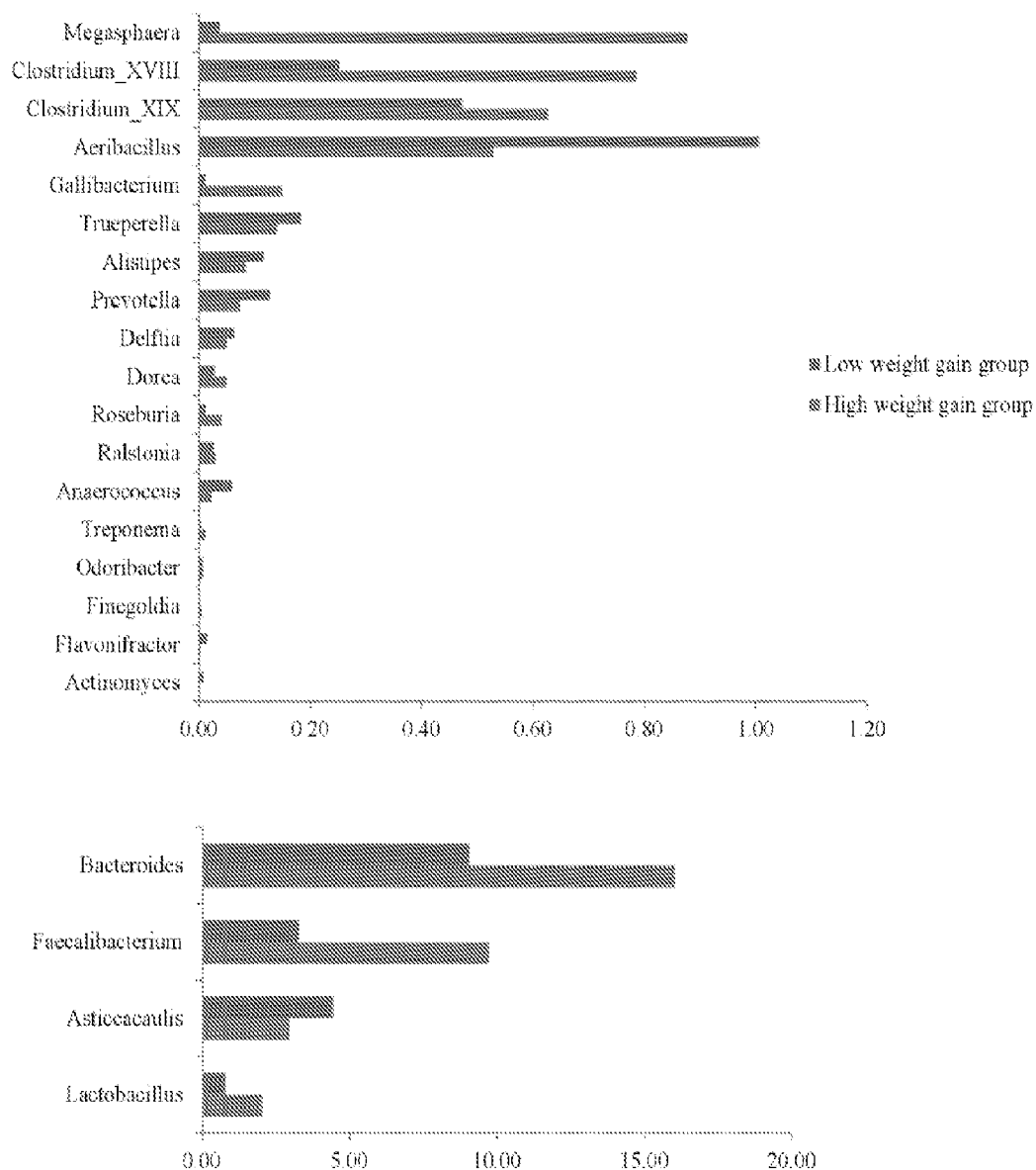
FIG. 8. Prevalence of genera that were found to be significant for the discriminant analysis of fecal microbiome by weight gain group during the first week of life.
Figure 9:
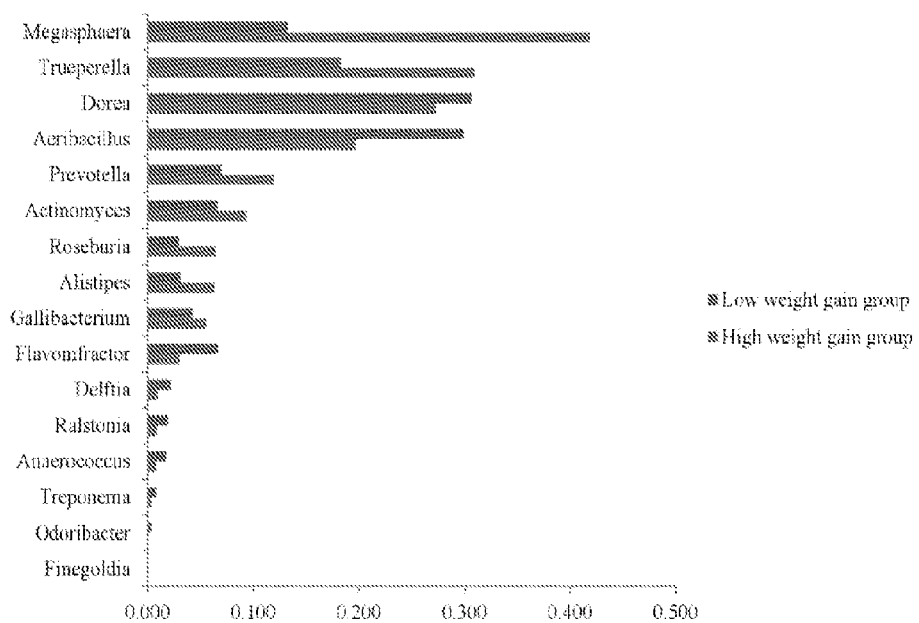
FIG. 9. Prevalence of genera that were found to be significant for the discriminant analysis of fecal microbiome by weight gain group during the second week of life.
Figure 9:
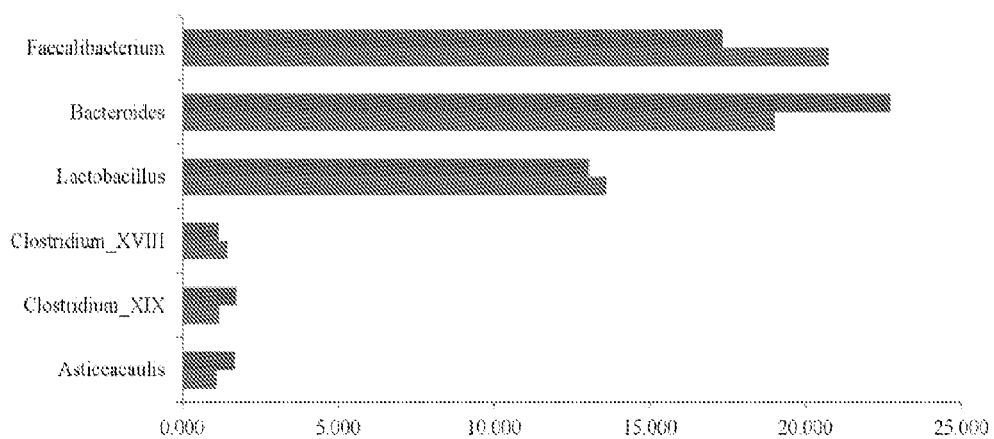

Differences in fecal microbiome by weight gain group for the first and second week of the calves' life derived from the discriminant analysis that used bacterial genus prevalence as covariates and the interaction of week (1 and 2) and weight gain (low and high) as the categorical variable are illustrated in FIG. 6b. Prevalence of genera significant for this analysis is presented in FIGS. 8 and 9.

Figure 10:
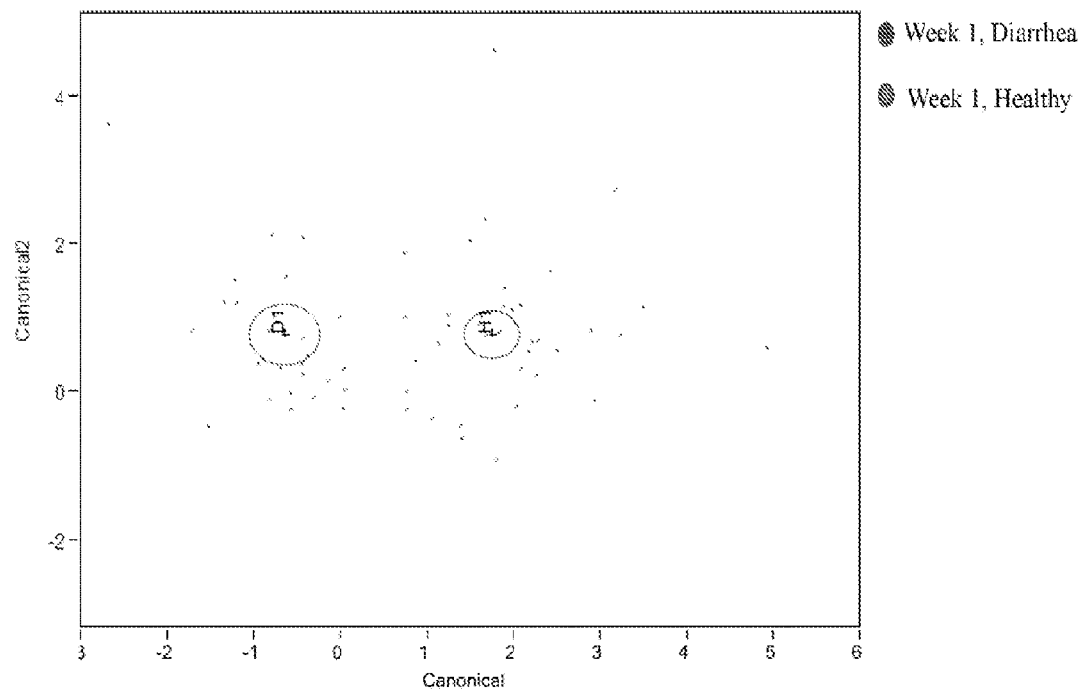
FIG. 10. Differences in fecal microbiome for the first week of the calves' life and for calves that suffered or not from diarrhea, derived from the discriminant analysis that used bacterial genus prevalence as covariates and diarrhea incidence as the categorical variable.
Figure 11:
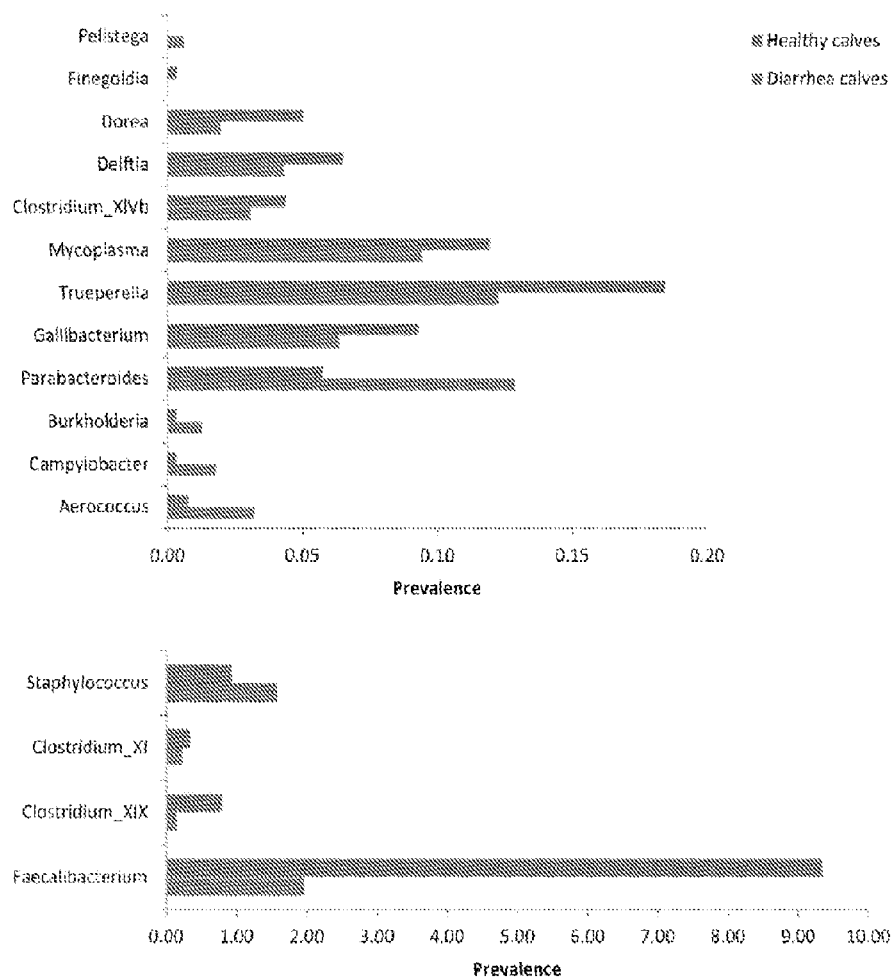
FIG. 11. Prevalence of genera significant for the discriminant analysis that used bacterial genus prevalence during the first week as covariates and diarrhea incidence as the categorical variable.

Differences in fecal microbiome for the first week of the calves' life and for calves that suffered or not from diarrhea, derived from the discriminant analysis that used bacterial genus prevalence as covariates and diarrhea incidence as the categorical variable are illustrated in FIG. 10. Prevalence of genera significant for this analysis is presented in FIG. 11.

Figure 12:
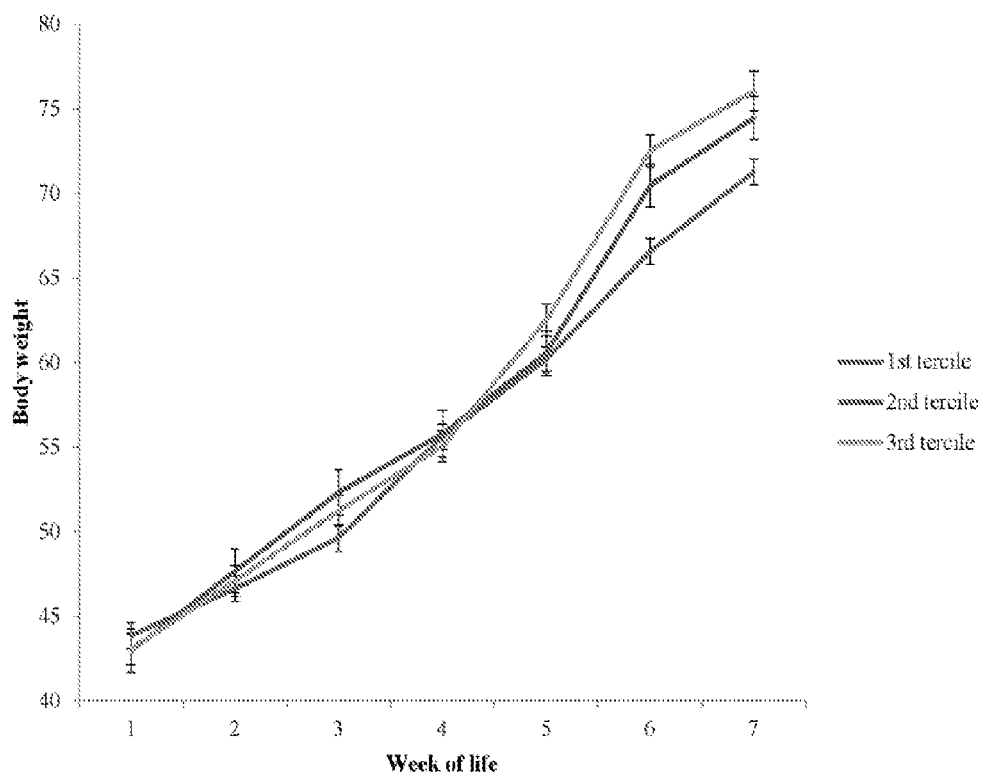
FIG. 12: Adjusted least square means of body weight by week of life as well as adjusted least square means of diarrhea incidence for different *Faecalibacterium* spp. terciles.
Figure 12:
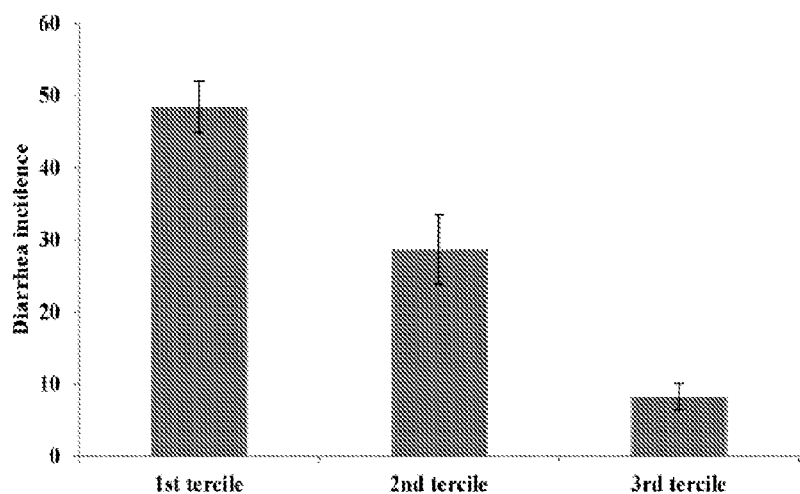

*Faecalibacterium* spp prevalence during the first week of life was found to have a significant effect on both body weight measurements and diarrhea incidence. Adjusted least square means of body weight by week of life as well as adjusted least square means of diarrhea incidence for different *Faecalibacterium* spp. terciles are presented in FIG. 12. Calves from the high prevalence tercile had an adjusted mean body weight of 76 kg at the seventh week of their life and an adjusted mean diarrhea incidence of 8.2% while calves from the low prevalence tercile had an adjusted mean body weight of 71.3 kg at the seventh week of their life and an adjusted mean diarrhea incidence of 48.4%. Sequences representative of the *Faecalibacterium* spp. were found to have a 100% match with sequences from *Faecalibacterium prausnitzii*.

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

The invention claimed is:

1. A method of improving weight gain, preventing diarrhea and/or improving feed efficiency in calves of less than two months of age comprising administering to said calves of less than two months of age a composition comprising one or more *Faecalibacterium* spp.

2. The method of claim 1, wherein said *Faecalibacterium* spp. is *Faecalibacterium prausnitzii*.

3. The method of claim 1, wherein said composition comprises one or more *Faecalibacterium* spp. in an amount effective to improve weight gain in said calves of less than two months of age.

4. The method of claim 1, wherein said composition comprises one or more *Faecalibacterium* spp. in an amount effective to provide prophylaxis against diarrhea in said calves of less than two months of age.

5. The method of claim 1, wherein said composition comprises one or more *Faecalibacterium* spp. in an amount effective to improve feed efficiency in said calves of less than two months of age.

6. The method of claim 1, wherein said composition is formulated as a powder, bolus, gel, drench, or capsule.

7. The method of claim 1, wherein said composition is provided as part of a milk replacer.

8. The method of claim 1, wherein said composition is coadministered with at least a second probiotic organism selected from the group consisting of *Lactobacillus acidophilus, L. lactis, L. plantarum, L. casei, Bacillus subtilis, B. lichenformis, Enterococcus faecium, Bifidobacterium bifidum, B. longum, B. thermophilum, Propionibacterium jensenii*, yeast, and combinations thereof.

9. The method of claim 1, wherein said composition is formulated with an additional additive selected from the group consisting of an energy substrate, a mineral, a vitamin, and combinations thereof.

10. A method of improving weight gain and/or improving feed efficiency in calves of less than two months of age comprising administering to said calves of less than two months of age a composition comprising one or more *Faecalibacterium* spp.

11. The method of claim 10, wherein said *Faecalibacterium* spp. is *Faecalibacterium prausnitzii*.

12. The method of claim 10, wherein said composition comprises one or more *Faecalibacterium* spp. in an amount effective to improve weight gain in said calves of less than two months of age.

13. The method of claim 10, wherein said composition comprises one or more *Faecalibacterium* spp. in an amount effective to improve feed efficiency in said calves of less than two months of age.

14. The method of claim 10, wherein said composition is formulated as a powder, bolus, gel, drench, or capsule.

15. The method of claim 10, wherein said composition is provided as part of a milk replacer.

16. The method of claim 10, wherein said composition is coadministered with at least a second probiotic organism selected from the group consisting of *Lactobacillus acidophilus, L. lactis, L. plantarum, L. casei, Bacillus subtilis, B. lichenformis, Enterococcus faecium, Bifidobacterium bifidum, B. longum, B. thermophilum, Propionibacterium jensenii*, yeast, and combinations thereof.

17. The method of claim 10, wherein said composition is formulated with an additional additive selected from the group consisting of an energy substrate, a mineral, a vitamin, and combinations thereof.

\* \* \* \* \*

SEQUENCE LISTING

```
<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(35)
<223> OTHER INFORMATION: n is a, c, g, or t

<400> SEQUENCE: 1
cgtatcgcct ccctcgcgcc atcagnnnnn nnnnntcaga gtttgatcct ggctcag       57

<210> SEQ ID NO 2
<211> LENGTH: 56
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (26)..(35)
<223> OTHER INFORMATION: n is a, c, g, or t

<400> SEQUENCE: 2
ctatgcgcct tgccagcccg ctcagnnnnn nnnnncatgc tgcctcccgt aggagt          56
```